(12) United States Patent
Martinez-Conde et al.

(10) Patent No.: US 8,348,428 B2
(45) Date of Patent: Jan. 8, 2013

(54) METHOD OF DETECTING NEUROLOGICAL DISEASE

(75) Inventors: Susana Martinez-Conde, Anthem, AZ (US); Stephen L. Macknik, Anthem, AZ (US); Xoana Troncoso, Phoenix, AZ (US); Jorge Otero-Millan, Phoenix, AZ (US)

(73) Assignee: Dignity Health, Phoenix, AZ (US)

( * ) Notice: Subject to any disclaimer, the term of this patent is extended or adjusted under 35 U.S.C. 154(b) by 97 days.

(21) Appl. No.: 12/740,008

(22) PCT Filed: Oct. 31, 2008

(86) PCT No.: PCT/US2008/082034
§ 371 (c)(1),
(2), (4) Date: Jul. 15, 2010

(87) PCT Pub. No.: WO2009/059167
PCT Pub. Date: May 7, 2009

(65) Prior Publication Data
US 2010/0277693 A1 Nov. 4, 2010

Related U.S. Application Data

(60) Provisional application No. 60/984,628, filed on Nov. 1, 2007.

(51) Int. Cl.
*A61B 3/14* (2006.01)
(52) U.S. Cl. ..................... 351/209; 351/246

(58) Field of Classification Search .............. 351/205, 351/209, 246, 210
See application file for complete search history.

(56) References Cited

U.S. PATENT DOCUMENTS 7,309,125 B2 * 12/2007 Pugach et al. ............... 351/201
2007/0013868 A1 1/2007 Pugach et al.

OTHER PUBLICATIONS

PCT Notification of Transmittal of the International Search Report and the Written Opinion of the International Searching Authority, or the Declaration, Jan. 29, 2009, (9 pages)—PCT/US08/82034.
Microsaccades as an overt measure of covert attention shifts, Ziad M. Hafed, et al., Vision Research 42 (2002) 2533-2545 (13 pages).

\* cited by examiner

*Primary Examiner* — Huy K Mai
(74) *Attorney, Agent, or Firm* — Husch Blackwell LLP

(57) ABSTRACT

A method and apparatus are provided for characterizing square wave jerks in the eye movements of a person, which may provide a powerful tool in the differential diagnosis of oculomotor and neurological disease. The method includes the steps of a) providing a sequence of saccades, b) identifying pairs of consecutive saccades of the sequence, c) determining whether each saccade of each identified pair is opposite the direction of the other saccade and, if not, then discarding the pair, d) determining whether a magnitude of each saccade of each identified pair is comparable and, if not, then discarding the pair, e) determining whether the pair of saccades of each identified pair are temporally related by a predetermined time period and, if not, then discarding the pair and f) collecting any remaining pairs of saccades as square wave jerks.

19 Claims, 5 Drawing Sheets

1ST SACCADE IN RED; ACCEPTABLE DIRECTIONS
OF 2ND SACCADE IN BLUE

AVG. MAGNITUDE OF 1ST
AND 2ND SACCADE

DIFFERENCE IN DIRECTION BETWEEN
THE 1ST AND THE 2ND SACCADE (DEG.)

RELATIVE MAGNITUDE DIFFERENCE
OF 1ST AND THE 2ND SACCADE (%)

INTER-SACCADIC INTERVAL(MS)

METHOD OF DETECTING NEUROLOGICAL DISEASE

The present invention claims the benefit of U.S. Provisional Patent Application No. 60/984,628 filed on Nov. 1, 2007.

FIELD OF THE INVENTION

The field of the invention relates to using eye movements as a way to identify neurological disease.

BACKGROUND OF THE INVENTION

The eye movements of people with neurological disease differ significantly from healthy people. Because of the importance of neurological disease, a need exists for better methods of evaluating such differences.

SUMMARY

A method and apparatus are provided for characterizing square wave jerks in the eye movements of a person, which may provide a powerful tool in the differential diagnosis of oculomotor and neurological disease. The method includes the steps of a) obtaining a sequence of saccades, b) identifying pairs of consecutive saccades of the sequence, c) determining whether each saccade of each identified pair is opposite the direction of the other saccade and, if not, then discarding the pair, d) determining whether the magnitude of each saccade of each identified pair is comparable and, if not, then discarding the pair, e) determining whether the pair of saccades of each identified pair are temporally related by a predetermined time period and, if not, then discarding the pair and f) collecting any remaining pairs of saccades as square wave jerks.

DETAILED DESCRIPTION OF AN ILLUSTRATED EMBODIMENT

The eyes do not stay perfectly still during visual fixation. Fixational eye movements and saccadic intrusions continuously change the position of the gaze.

Microsaccades are rapid, small-magnitude involuntary saccades that occur several times each second during fixation; microsaccades counteract visual fading and generate strong neural transients in the early visual system. Microsaccades may also drive perceptual flips in binocular rivalry. Microsaccade rates and directions are moreover modulated by attention, and thus generate rich spatio-temporal dynamics. Further, fixational eye movements as a whole enhance fine spatial acuity.

The most common type of saccadic intrusion is referred to as a square wave jerk (SWJ). SWJs are characterized by one small horizontal saccadic movement that moves the eye away from the fixation target, followed by a corrective saccade towards the target shortly thereafter. SWJs are prevalent in some neurological diseases such as progressive supranuclear palsy (PSP). However, they are also common in normal subjects. A process is described herein that automatically identifies SWJs in the eye movements of a person, during visual fixation of a small target. The results show that SWJs are common in both PSP patients and healthy subjects. However, several SWJ parameters (e.g., SWJ rates, magnitudes, percentage of small saccades that are part of SWJs, average inter-saccadic intervals for the SWJs, saccadic rates, saccadic peak velocities within SWJs, standard deviation of the direction difference between pairs of saccades in the SWJs, standard deviation of the difference between the horizontal and the direction of the saccades in the SWJs) have been found to be different in the PSP group. Thus the objective characterization of SWJs may provide a powerful tool in the differential diagnosis of oculomotor disease.

Although people spend about 80% of their waking lives fixating their gaze, the contribution of impaired fixational eye movements to vision loss has been overlooked as a potential clinical malady. This gap in knowledge has prevented the field from developing new treatments and diagnostics to ameliorate visual deficits due to impaired fixational eye movements.

In general, a healthy subject or a patient will fixate on a target while his/her eye movements are recorded with an eye tracking system. Any eye tracking system available can be used for this purpose: video tracking, scleral search coil, etc. The temporal and spatial resolution of the eye tracking systems will ideally be high enough to allow the detection of small saccades during fixation. A sampling rate of 500 Hz or higher is recommended, although small saccades can nevertheless be detected with lower rates at the expense of non optimal performance.

Figure 1:
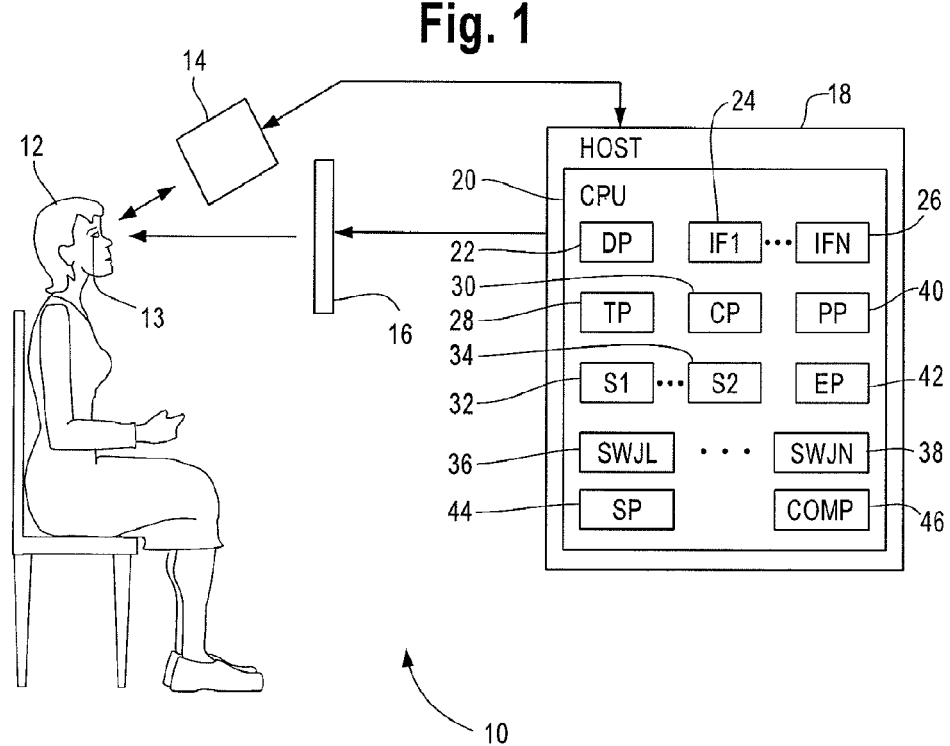
FIG. 1 is a block diagram of a system for detecting and characterizing square wave jerks in the eye movements of a person to diagnose neurological disease, shown generally in accordance with an illustrated embodiment of the invention.
Figure 3:
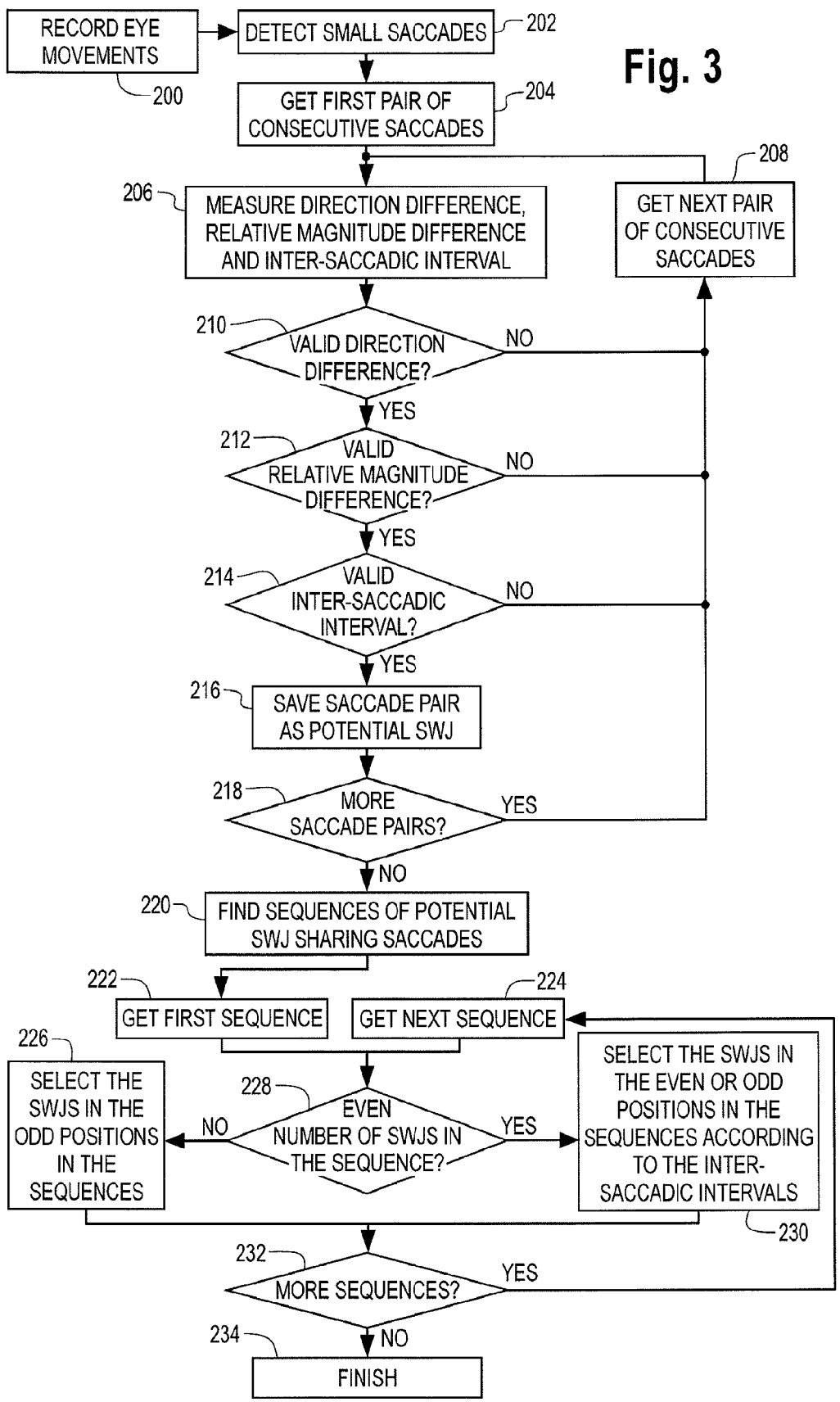
FIG. 3 is a flow chart of steps that may be followed by the system of FIG. 1.

FIG. 1 shows an example of an eye tracking system 10 for detecting eye movement under an illustrated embodiment of the invention. FIG. 3 is a flow chart of steps that may be followed by the system 10. Included within the system 10 may be an eye tracking device 14, such as the EyeLink II by SR Research (http://www.sr-research.com/fixed_tech_spec.php) or other equivalent eye tracking systems such as the IVIEW™ HI-SPEED 1250 tracking system by SensoMotoroic Instruments (http://www.smivision.com/en/eye-gaze-tracking-systems/products/iview-x-hi-speed.html). Also included within the system 10 may be a display 16 and host 18.

The objective of the data collection of the system 10 is to automatically and objectively detect square wave jerks (SWJs) present in the eye movement trace. SWJs are characterized by one small horizontal saccade that moves the eye away from the fixation target, followed by a corrective saccade towards the target shortly thereafter.

Figure 2:
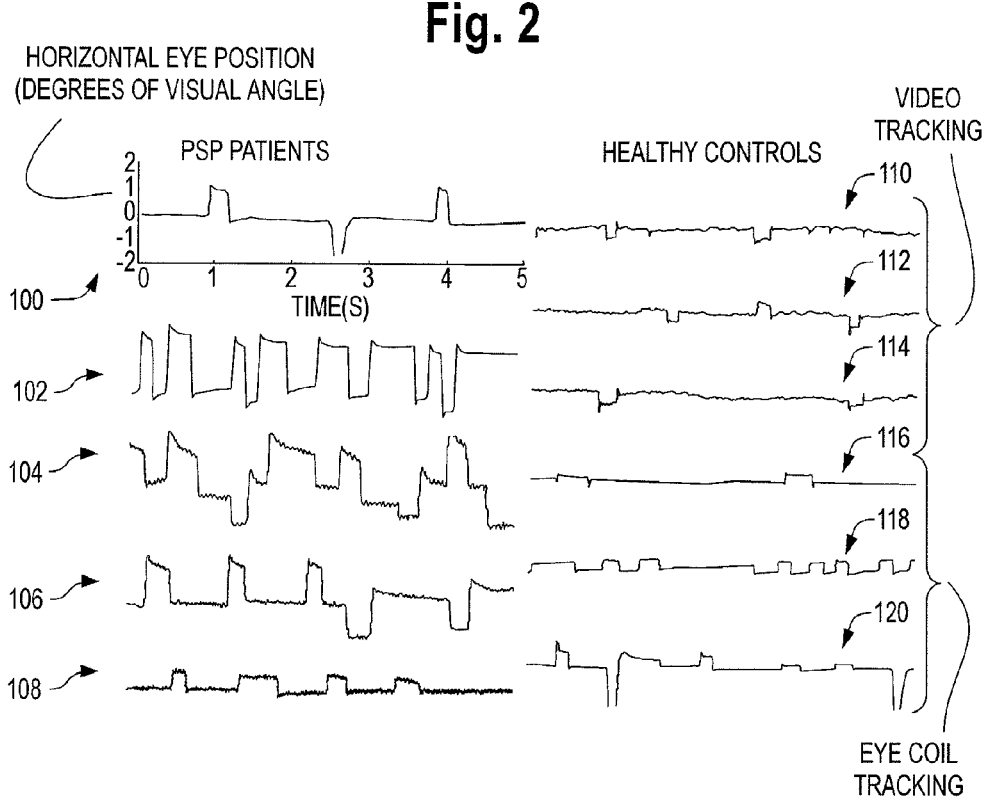
FIG. 2 is a number of graphs of saccades of patients and healthy persons.

FIG. 2 provides examples of eye movement recordings for PSP patients and healthy subjects. A first graph 100 shows an example of horizontal eye position in degrees of visual angle versus time. Graphs 102, 104, 106, 108 provide other examples of eye position versus time for a group of PSP patients, while graphs 110, 112, 114, 116, 118 and 120 provide examples of eye position for healthy test subjects.

A display processor 22 within a controller 20 of the system 10 will present the fixation target to a person 12 on the display 16.

As the person 12 fixates in the target on the display 16, the eye tracking device 14 detects and records 200 the position and movement of the eyes 13 of the person 12. A tracking processor 28 within the host 18 may receive the position of the eyes 13 and store it for later transfer to a saccade processor 30. The saccade processor 30 may receive the eye position measurements, may detect 202 substantially all the consecutive pairs of saccades (up to a certain maximum magnitude, for instance, 5 degrees). Any method to detect small saccades can be used by the saccade processor 30. Two main algorithms have been used in the literature: the Martinez-Conde and Macknik algorithm (Martinez-Conde, Macknik, Hubel (2000) Nature Neuroscience 3: 251-258) and Engbert algorithm (Engbert, Kliegl (2003) Vision Res 43:1035-1045).

The first step of the Martinez-Conde and Macknik process that may be used by the saccade processor 30 is the differentiation of the data (horizontal and vertical position), so that each element represents the instantaneous velocity of the eye in horizontal and vertical space, then data may then be smoothed with a 31 ms-wide unweighted boxcar filter to reduce noise. Then, the direction and size of the motion between each two samples is calculated. The size of the motion represents the velocity of movement in polar coordinates and the direction is differentiated to obtain the rate-of-turn indicator. The saccade processor 30 determines that the eye is moving when the polar velocity is more than 3° per s and the rate-of-turn is smaller than 15°. Finally only detected eye movements of more than 3 arcmin and less than 2° are considered saccades.

Under the Engbert process, the saccade processor 30 may first transform the time series of eye positions into velocities in accordance with the equation $$\vec{v}_n = \frac{\vec{x}_{n+2} + \vec{x}_{n+1} - \vec{x}_{n-1} - \vec{x}_{n-2}}{6\Delta t},$$

which represents a moving average of velocities over 5 data samples in order to suppress noise. As a consequence of the random orientations of the velocity vectors during fixation, the resulting mean value of noise is effectively zero. A multiple of the standard deviation of the velocity distribution is used as the detection threshold. Detection thresholds are computed independently for horizontal and vertical components and separately for each trial, relative to the noise level.

Typical values for the threshold are 4, 5 or 6 times the standard deviation of the velocity. Therefore, the process used by the saccade processor 30 is robust with respect to different noise levels between different trials and subjects. Additionally, minimum saccade duration of 8 or 12 ms is required to further reduce noise. Finally, only binocular saccades are used, that is, saccades with at least 1 sample of overlap between the two eyes.

The principal advantage of the Engbert algorithm is that it adapts to the level of noise of the data. However, while this improves its performance in noisy situations it can produce non optimal results in low noise conditions where the Martinez-Conde and Macknik algorithm behaves better.

As the saccades 32, 34 are identified (or after), a pairing processor 40 may determine and combine consecutive pairs of associated saccades 32, 34 into potential SWJs 36, 38. The pairing processor 40 may get a first pair of consecutive saccades 204 and measure a direction difference, a relative magnitude difference and an inter-saccade difference 206. The pairing processor 40 may use three criteria 210, 212, 214 to determine whether a pair of saccades 32, 34 is a SWJ 36, 38. If a pair of saccades 32, 34 does not meet each of the three criterion, then the pair may be discarded.

Figure 4A:
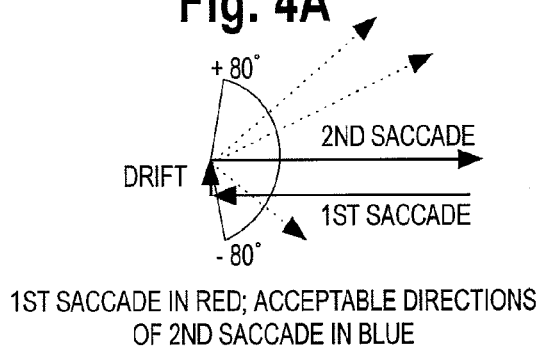
FIG. 4 graphically depicts steps in identifying square wave jerks that may be followed by the system of FIG. 1.

The First criterion requires that the two consecutive saccades 32, 34 should have (loosely) opposite directions. In a perfect SWJ this difference would be exactly 180°. Allowing for some variability, a pair of saccades meets this criterion 210 if the direction difference is in the range 180°±80°. (See FIGS. 4A and 4D).

Figure 4B:
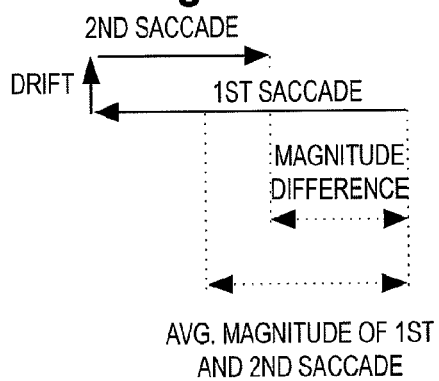
Figure 4C:
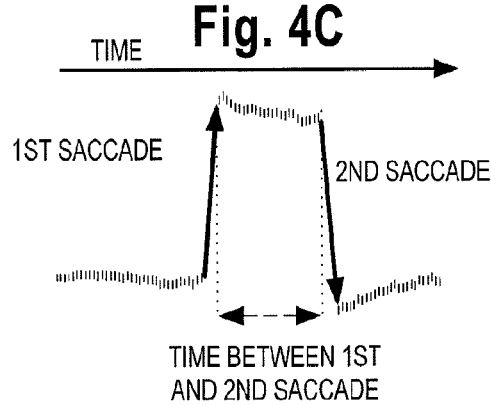
Figure 4D:
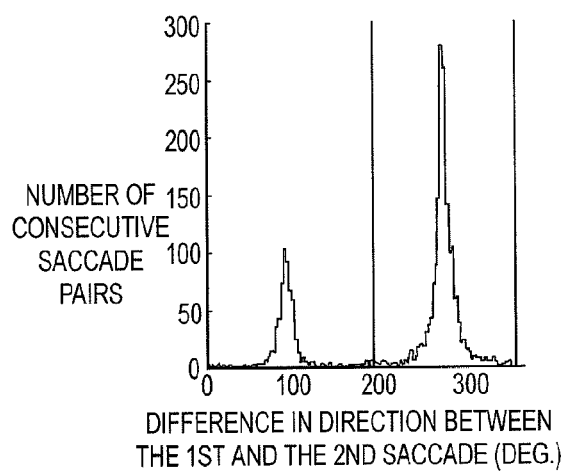
Figure 4E:
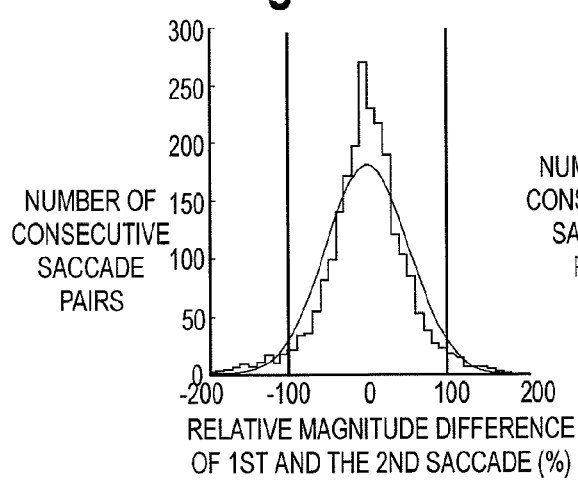

The second criterion 212 is that the two consecutive saccades 32, 34 should have similar magnitudes as shown in FIGS. 4B and 4E. A disimilarity index may be objectively calculated as the magnitude difference between the 1st and the 2nd saccade divided by the average magnitude of both saccades (expressed in percent terms) by the following equation, $$\frac{\text{magnitude of } 1^{st} \text{ saccade} - \text{magnitude of } 2^{nd} \text{ saccade}}{\text{average magnitude of } 1^{st} \text{ and } 2^{nd} \text{ saccade}} \times 100$$

An ideal SWJ (where the two saccades have equal magnitudes) would have an index of 0%. A pair of saccades is considered a SWJ if the index is in the range ±100%.

The third criterion 214 may require that the two consecutive saccades should have Inter-Saccadic Interval (ISI) (between the end of the 1st saccade and the beginning of the 2nd saccade) in the range 70 ms-650 ms. (See FIGS. 4C and 4F).

Once the saccade processor 30 has processed a saccade pair, the processor 30 may determined if there are any more saccade pairs 218. If so, then the saccade processor 30 retrieves the next pair 208 of the sequence and the process repeats.

Figure 4F:
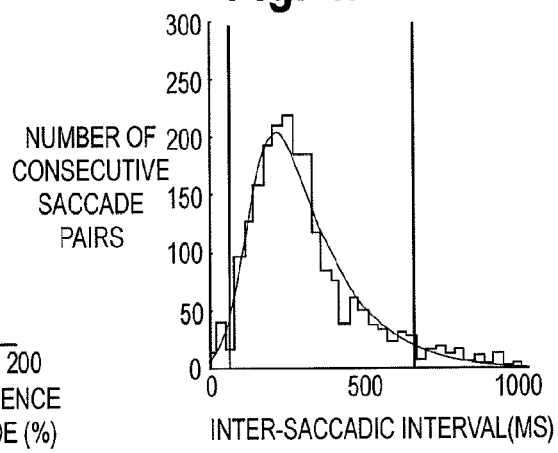
Figure 5A:
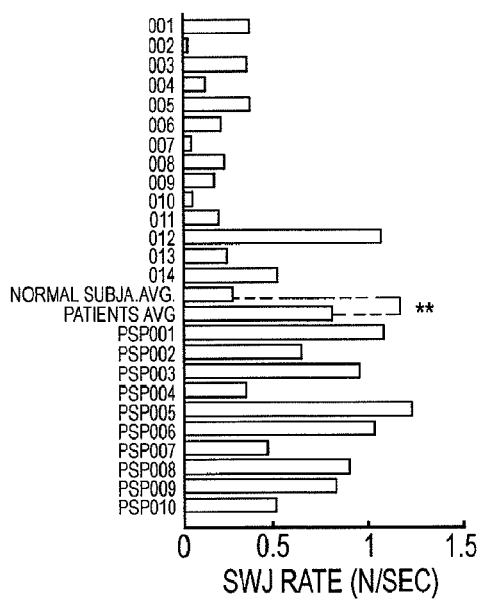
FIG. 5 compares statistics of patients and healthy persons that may be provided by the system of FIG. 1.
Figure 5B:
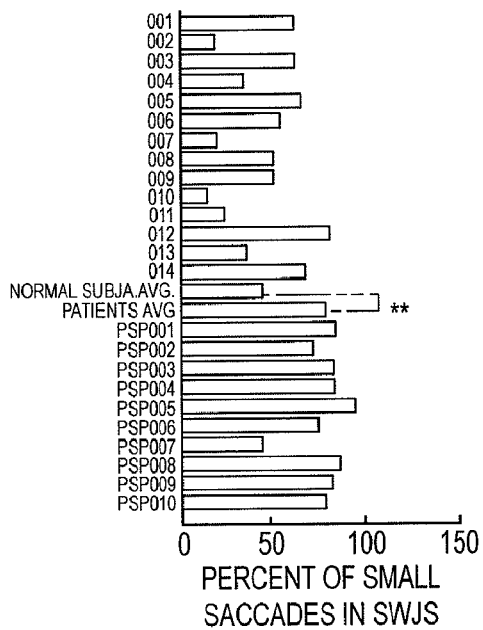
Figure 5C:
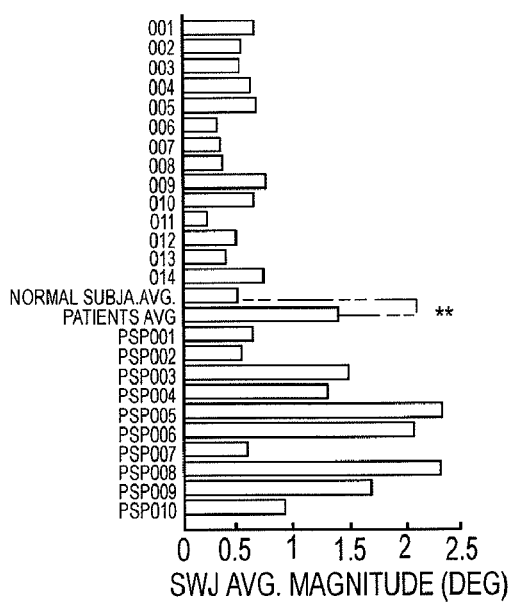
Figure 5D:
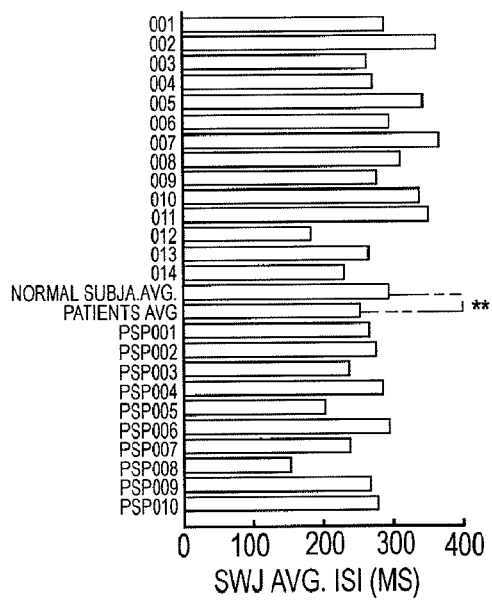
Figure 5E:
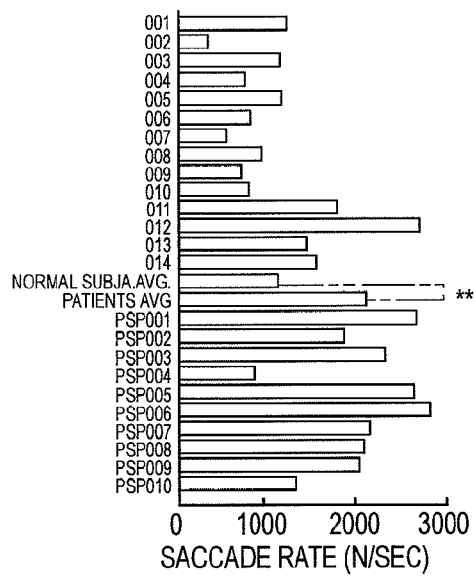
Figure 5F:
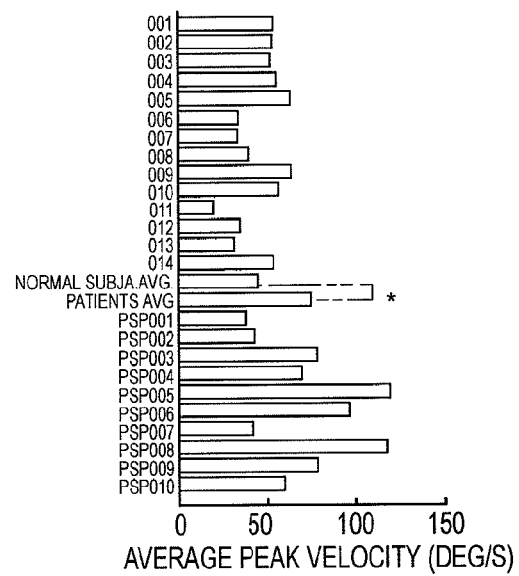
Figure 5G:
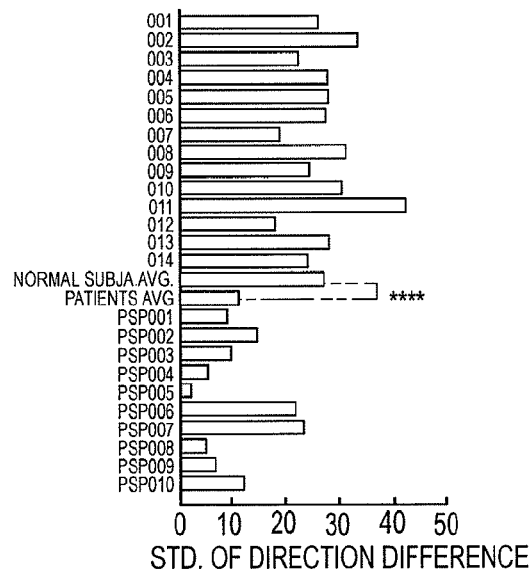
Figure 5H:
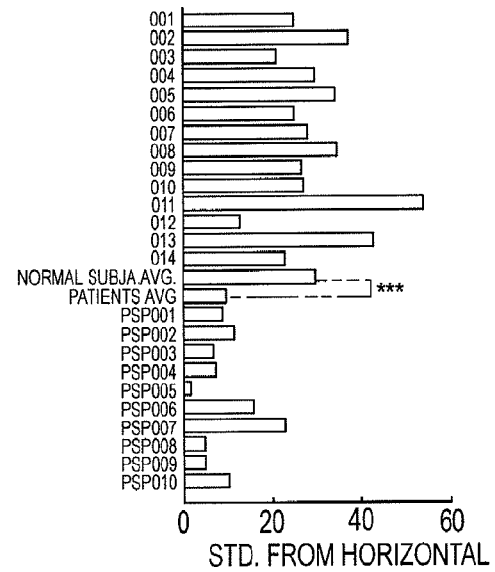

The specific numeric values for the three different criteria were optimized based on a data from a set of PSP patients (see FIGS. 4D, 4E, 4F). The system 10 could also be used with other criteria values where the other criteria values show a better performance.

As a last step, an elimination processor 42 may locate sequences of potential SWJs sharing saccades 220 and eliminate the SWJs 36, 38 that share saccades 32, 34. The result of the previous step is a sequence of pairs of saccades that meet the initially defined SWJ criteria. However, it is possible that in some cases that these pairs are linked by a shared saccade. To solve this problem and have saccades that are only part of a unique SWJ, the following rule may be used: if the number of SWJs linked by shared saccades is odd, then the SWJs in even positions in the sequence of SWJs are discarded. That is one way to ensure that all the saccades are part of only one SWJ.

If the number is even, then it is impossible to achieve this result and at least one saccade will not be part of any SWJ. In this case the odd or even SWJs may be discarded depending upon which choice provides a shorter average inter-saccadic interval.

As such, the elimination processor 42 may retrieve a first sequence 222 of potential SWJs and determine the number of potential SWJs that share a saccade. If the number of SWJs with shared saccades is even 228, then the elimination processor 42 selects the SWJs in the even or odd positions in the sequence according to the inter-saccadic intervals 230. If not, then the elimination processor 42 selects the SWJs in the odd positions of the sequence 226. If there are any more sequences 232, the process repeats. If not, then the elimination process ends 234.

Following identification of SWJs 36, 38, that meet the appropriate criteria, the remaining SWJs 36, 38 may be transferred to a statistics processor 44. Within the statistics processor 44, the SWJs 36, 38 of PSP patients can be compared with healthy subjects. FIG. 5 provides SWJ parameter comparison between a population of healthy subjects and a population of PSP patients. The system 10 can be used to automatically compute several SWJ parameters that can help to determine whether a person is healthy or has certain neurological diseases. In all the panels of FIG. 5, the upper rows (labeled "001" through "014") correspond to respective healthy subjects and the lower rows (labeled "PSP001" through "PSP010") correspond to respective PSP patients. The horizontal bar (labeled "Normal subjs.avg.") is the average of the healthy subjects' population and the horizontal bar (labeled "Patients.avg.") is the average of the PSP patients' population respectively.

The parameters represented in each panel of FIG. 5 are (from left to right and top to bottom): (A) Number of SWJ per second; (B) Percentage of small saccades that are part of SWJs; (C) Average magnitude of the saccades that are part of SWJs; (D) Average inter-saccadic interval for the SWJs; (E) Number of saccades per second; (F) Average peak velocity of the saccades in SWJs; (G) Standard deviation of the direction difference and (H) Standard deviation of the difference between the horizontal and the direction of the saccades in the SWJs. All the parameters (with the exception of the inter-saccadic interval) are significantly different between the two populations (two-tailed t-test).

Any of a number of the statistics of FIG. 5 may be the basis of a screening test for detecting PSP. For example, the standard deviation of direction difference in FIG. 5 (G) shows a greater than a two to one difference between the PSP patients and normal subjects. In this case, the standard deviation of direction difference of a subject 12 tested with the system 10 may be compared within a comparator 46 with the standard deviation of direction difference of a normal subjects to detect PSP. Other statistics of FIG. 5 may be used in a similar manner.

A specific embodiment of method and apparatus for detecting and characterizing square wave jerks in the eye movements of a person, which may provide a powerful tool in the differential diagnosis of oculomotor and neurological disease, has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

The invention claimed is:

1. A method of detecting and characterizing square wave jerks (SWJs) in the eye movements of a person, for the diagnosis of progressive supranuclear palsy (PSP) disease comprising:
   a) providing an apparatus for obtaining a sequence of saccades and obtaining a sequence of saccades from both eyes of a person;
   b) identifying via an apparatus pairs of consecutive saccades of the sequence;
   c) determining via an apparatus whether each saccade of each identified pair is opposite the direction of the other saccade and, if not, then discarding the pair;
   d) determining via an apparatus whether a magnitude of each saccade of each identified pair is comparable and, if not, then discarding the pair;
   e) determining via an apparatus whether the pair of saccades of each identified pair are temporally related by a predetermined time period and, if not, then discarding the pair;
   f) collecting via an apparatus any remaining pairs of saccades as square wave jerks;
   h) using an apparatus to determine one or more of the following parameters:
      (A) the number of SWJs per second;
      (B) the percentage of small saccades that are part of SWJs;
      (C) the average magnitude of the saccades that are part of SWJs;
      (D) the number of saccades per second;
      (E) the average peak velocity of the saccades in SWJs;
      (F) the standard deviation of the direction difference; and
      (G) the standard deviation of the difference between the horizontal and direction of the saccades in the SWJs; and
   h) comparing the one or more determined parameter with the parameter for a healthy person, whereby a statistical difference between the parameters indicates the presence of PSP.

2. The method of detecting and characterizing square wave jerks as in claim 1 further comprising defining the opposite direction of the saccades in the pairs as 180 degrees, plus or minus 80 degrees.

3. The method of detecting and characterizing square wave jerks as in claim 1 further comprising defining the magnitude of each saccades in the pairs comparable as the dissimilarity index is in the range ±100%.

4. The method of detecting and characterizing square wave jerks as in claim 1 further comprising defining the inter saccadic interval between the two saccades in the pair as the range 70 ms-650 ms.

5. The method of detecting and characterizing square wave jerks as in claim 1 wherein the step of providing the sequence of saccades further comprises identifying any pairs of saccades of the sequence that share a saccade and if the number identified pairs is an odd number, then discarding the pairs of the sequence in even positions within the sequence.

6. The method of detecting and characterizing square wave jerks as in claim 1 wherein the step of providing the sequence of saccades further comprises identifying any pairs of saccades of the sequence that share a saccade and if the number identified pairs is an even number, then discarding either the odd or even pairs of the sequence depending upon which provides a relatively longer average inter-saccadic interval.

7. The method of detecting and characterizing square wave jerks as in claim 1, wherein a single apparatus is utilized.

8. An apparatus for detecting and characterizing square wave jerks (SWJs) comprising:
   apparatus that obtains a sequence of saccades from a person;
   apparatus that identifies a first pair of consecutive saccades of the sequence;
   apparatus that determines whether the pair of saccades are opposite in direction and, if not, then discards the pair;
   apparatus that determines whether a magnitude of each saccade of the pair is comparable and, if not, then discards the pair;
   apparatus that determines whether the pair of saccades are temporally related by a predetermined time period and, if not, then discards the pair;
   apparatus that forms a square wave jerk sequence from the pairs of saccades; and apparatus that compares at least one of the number of SWJs per second, the percentage of small saccades that are part the SWJ sequence, the average magnitude of the saccades that are part of the SWJ sequence, the number of saccades per second, the average peak velocity of the saccades of the SWJ sequence, the standard deviation in the direction difference and the standard deviation of the difference between the horizontal and direction of the saccades of the SWJ sequence with a corresponding parameter of a healthy population of persons.

9. The apparatus for detecting and characterizing square wave jerks as in claim 8 further comprising defining the opposite direction of the pairs of saccades as 180 degrees, plus or minus 80 degrees.

10. The apparatus for detecting and characterizing square wave jerks as in claim 8 further comprising defining the magnitude of each saccades in the pairs comparable as the dissimilarity index is in the range ±100%.

11. The apparatus for detecting and characterizing square wave jerks as in claim 8 further comprising defining the inter saccadic interval between the two saccades in the pair as the range 70 ms-650 ms.

12. The apparatus for detecting and characterizing square wave jerks as in claim 8 wherein the means for providing the sequence of SWJs further comprises means for identifying any pairs of saccades of the sequence that share a saccade and if the number identified pairs is an odd number, then discarding the pairs of the sequence in even positions within the sequence.

13. The apparatus for detecting and characterizing square wave jerks as in claim 8 wherein the means for providing the sequence of SWJs further comprises means for identifying any pairs of saccades of the sequence that share a saccade and if the number identified pairs is an even number, then discarding either the odd or even pairs of the sequence depending upon which provides a relatively longer average inter-saccadic interval.

14. An apparatus for detecting and characterizing square wave jerks (SWJs) in a person comprising:
   a saccade processor that provides a sequence of saccades from measured eye movements of a person;
   a pairing processor that identifies a first pair of consecutive saccades of the sequence, that determines whether the two saccades in the pair have an opposite, horizontal direction and, if not, then discarding the pair, that determines whether a magnitude of each saccade of the pair is comparable and, if not, then discarding the pair, that determines whether the pair of saccades are temporally related by a predetermined time period and, if not, then discarding the pair and that forms a square wave jerk sequence from the pairs of saccades; and
   a statistics processor that compares at least one of the number of SWJs per second, the percentage of small saccades that are part the SWJ sequence, the average magnitude of the saccades that are part of the SWJ sequence, the number of saccades per second, the average peak velocity of the saccades of the SWJ sequence, the standard deviation in the direction difference and the standard deviation of the difference between the horizontal and direction of the saccades of the SWJ sequence with a corresponding parameter of a healthy population of persons.

15. The apparatus for detecting and characterizing square wave jerks in claim 14 wherein the opposite direction further comprises the pairs of saccades having an angle difference of 180 degrees, plus or minus 80 degrees.

16. The apparatus for detecting and characterizing square wave jerks in claim 14 wherein the opposite direction further comprises the magnitudes of the pairs of saccades having a dissimilarity index of ±100%.

17. The apparatus for detecting and characterizing square wave jerks in claim 14 wherein the opposite direction further comprises the inter saccadic interval between the two saccades in the pair being in the range 70 ms-650 ms.

18. The apparatus for detecting and characterizing square wave jerks as in claim 14 wherein the pairing processor further comprises an elimination processor that identifies any pairs of saccades of the sequence that share a saccade and if the number identified pairs is an odd number, then discards the pairs of the sequence in even positions within the sequence.

19. The apparatus for detecting and characterizing square wave jerks as in claim 14 wherein the pairing processor further comprises an elimination processor that identifies any pairs of saccades of the sequence that share a saccade and if the number identified pairs is an even number, then discards either the odd or even pairs of the sequence depending upon which provides a relatively longer average inter-saccadic interval.

* * * * *